US012342989B2

(12) United States Patent
Laughlin et al.

(10) Patent No.: US 12,342,989 B2
(45) Date of Patent: Jul. 1, 2025

(54) OPTICAL FIBER SENSOR SYSTEM

(71) Applicant: The Boeing Company, Chicago, IL (US)

(72) Inventors: Brian Dale Laughlin, Wichita, KS (US); Dane Brian Laughlin, Wichita, KS (US); Madison Lauryn Laughlin, Wichita, KS (US)

(73) Assignee: The Boeing Company, Chicago, IL (US)

( * ) Notice: Subject to any disclaimer, the term of this patent is extended or adjusted under 35 U.S.C. 154(b) by 1694 days.

(21) Appl. No.: 16/428,132

(22) Filed: May 31, 2019

(65) Prior Publication Data

US 2020/0375438 A1 Dec. 3, 2020

(51) Int. Cl.
*A61B 1/04* (2006.01)
*A61B 5/00* (2006.01)
*G01N 21/95* (2006.01)

(52) U.S. Cl.
CPC ............... *A61B 1/041* (2013.01); *A61B 5/42* (2013.01); *G01N 21/9508* (2013.01)

(58) Field of Classification Search
CPC ....... A61B 1/041; A61B 5/42; A61B 1/00–32; G01N 21/9508
See application file for complete search history.

(56) References Cited

U.S. PATENT DOCUMENTS

| 5,323,856 | A | | 6/1994 | Davis et al. | |
|---|---|---|---|---|---|
| 5,808,779 | A | * | 9/1998 | Weis | G01H 9/004 |
| | | | | | 359/290 |
| 5,984,860 | A | * | 11/1999 | Shan | A61B 1/041 |
| | | | | | 600/116 |
| 6,374,746 | B1 | | 4/2002 | Fiske | |
| 6,387,043 | B1 | * | 5/2002 | Yoon | A61B 17/3494 |
| | | | | | 600/129 |
| 6,460,460 | B1 | * | 10/2002 | Jasper, Jr. | F42C 11/00 |
| | | | | | 102/213 |
| 6,936,003 | B2 | * | 8/2005 | Iddan | A61B 5/0031 |
| | | | | | 600/101 |

(Continued)

FOREIGN PATENT DOCUMENTS

| CN | 101849814 A | 10/2010 |
|---|---|---|
| CN | 205814326 U | 12/2016 |
| WO | 2004091361 A2 | 10/2004 |

OTHER PUBLICATIONS

Extended European Search Report, dated Jul. 20, 2020, regarding Application No. EP20175491.8, 10 pages.

(Continued)

*Primary Examiner* — Anh Tuan T Nguyen
*Assistant Examiner* — Jae K Woo
(74) *Attorney, Agent, or Firm* — Yee & Associates, P.C.

(57) ABSTRACT

A method, apparatus, and system for delivering an optical sensor. A capsule is placed into a tube system, wherein an optical fiber is stored within the capsule. The capsule is moved through the tube system. The optical fiber is unfurled as the capsule travels through a tube system. Optical signals are sent through the optical fiber from a proximal end of the optical fiber. Response optical signals occurring in response to the optical signals sent through the optical fiber are detected. Sensor data is transmitted based on the response optical signals detected by the optical system.

39 Claims, 6 Drawing Sheets

(56) References Cited

U.S. PATENT DOCUMENTS

| | | | |
|---|---|---|---|
| 7,189,958 B2 * | 3/2007 | Spillman, Jr. | G01D 5/35341 |
| | | | 385/13 |
| 7,226,410 B2 * | 6/2007 | Long | A61M 25/0116 |
| | | | 604/528 |
| 7,781,724 B2 * | 8/2010 | Childers | A61B 1/00165 |
| | | | 250/227.14 |
| 8,187,174 B2 | 5/2012 | Wang | |
| 8,780,339 B2 * | 7/2014 | Udd | A61B 50/10 |
| | | | 356/73.1 |
| 8,812,081 B2 * | 8/2014 | Li | G01S 17/88 |
| | | | 128/207.14 |
| 8,864,655 B2 * | 10/2014 | Ramamurthy | A61B 5/066 |
| | | | 600/117 |
| 9,161,684 B2 * | 10/2015 | Seibel | A61B 5/1455 |
| 9,500,756 B2 * | 11/2016 | Barfoot | G01V 1/001 |
| 9,693,707 B2 * | 7/2017 | Chan | A61B 5/061 |
| 9,968,290 B2 | 5/2018 | Belson | |
| 10,646,109 B1 * | 5/2020 | Freeman | A61B 1/00154 |
| 10,736,494 B2 * | 8/2020 | Gora | A61B 5/0086 |
| 11,039,890 B2 * | 6/2021 | Cole | A61M 25/104 |
| 2003/0023150 A1 * | 1/2003 | Yokoi | H04N 5/2252 |
| | | | 348/E5.026 |
| 2004/0111020 A1 * | 6/2004 | Long | A61B 1/00156 |
| | | | 600/407 |
| 2004/0176664 A1 * | 9/2004 | Iddan | A61B 1/00156 |
| | | | 600/101 |
| 2005/0029437 A1 * | 2/2005 | Hasegawa | G02B 23/2407 |
| | | | 250/226 |
| 2006/0140531 A1 * | 6/2006 | Shin | A61B 1/009 |
| | | | 385/5 |
| 2006/0155174 A1 * | 7/2006 | Glukhovsky | A61B 1/00036 |
| | | | 600/300 |
| 2006/0278240 A1 * | 12/2006 | Spillman, Jr. | G01D 5/35306 |
| | | | 128/898 |
| 2007/0299309 A1 * | 12/2007 | Seibel | A61N 5/0603 |
| | | | 600/117 |
| 2008/0071139 A1 * | 3/2008 | Fujita | A61B 1/00158 |
| | | | 600/103 |
| 2008/0188766 A1 | 8/2008 | Gertner | |
| 2008/0272931 A1 * | 11/2008 | Auzerais | E21B 33/16 |
| | | | 356/477 |
| 2009/0234203 A1 * | 9/2009 | Arita | A61B 5/073 |
| | | | 600/302 |
| 2010/0249506 A1 * | 9/2010 | Prisco | A61B 1/00009 |
| | | | 600/117 |
| 2010/0249507 A1 * | 9/2010 | Prisco | A61B 1/0005 |
| | | | 600/117 |
| 2010/0268025 A1 | 10/2010 | Belson | |
| 2011/0208011 A1 * | 8/2011 | Ben-Horin | A61B 1/00156 |
| | | | 600/300 |
| 2012/0165792 A1 * | 6/2012 | Ortiz | A61B 1/00148 |
| | | | 604/890.1 |
| 2013/0184544 A1 * | 7/2013 | Su | A61B 5/0095 |
| | | | 600/407 |
| 2013/0184555 A1 * | 7/2013 | Chen | A61B 5/0088 |
| | | | 600/407 |
| 2013/0204085 A1 * | 8/2013 | Alexander | A61B 1/00158 |
| | | | 600/101 |
| 2013/0231530 A1 | 9/2013 | Lien et al. | |
| 2013/0231533 A1 * | 9/2013 | Papademetriou | A61J 15/0007 |
| | | | 600/101 |
| 2013/0310643 A1 * | 11/2013 | Gora | A61B 1/06 |
| | | | 600/109 |
| 2013/0310685 A1 * | 11/2013 | Chan | A61B 34/20 |
| | | | 600/424 |
| 2014/0219056 A1 * | 8/2014 | Samson | E21B 47/13 |
| | | | 367/81 |
| 2014/0243660 A1 * | 8/2014 | Klinder | A61B 6/12 |
| | | | 600/424 |
| 2014/0309526 A1 * | 10/2014 | Margallo Balbas | |
| | | | A61B 1/00172 |
| | | | 600/109 |
| 2015/0268416 A1 * | 9/2015 | Coffey | G01D 5/268 |
| | | | 250/227.11 |
| 2016/0242737 A1 * | 8/2016 | Zhou | A61B 1/00082 |
| 2016/0252414 A1 * | 9/2016 | Preston | H04B 10/0775 |
| | | | 356/32 |
| 2016/0345809 A1 * | 12/2016 | Tearney | A61B 5/0066 |
| 2017/0290693 A1 * | 10/2017 | Nelson | A61B 5/4887 |
| 2018/0160884 A1 * | 6/2018 | Tsai | A61B 1/041 |
| 2019/0010803 A1 | 1/2019 | Purkis | |
| 2019/0145933 A1 | 5/2019 | Feng et al. | |
| 2019/0261840 A1 * | 8/2019 | Gora | A61B 1/00172 |
| 2020/0150301 A1 * | 5/2020 | Hallemeier | G01H 9/004 |
| 2020/0196873 A1 * | 6/2020 | Ntziachristos | A61B 1/00147 |
| 2021/0128125 A1 | 5/2021 | Sitti et al. | |
| 2021/0169314 A1 * | 6/2021 | Tsai | A61B 1/041 |
| 2021/0169352 A1 * | 6/2021 | Duval | A61B 5/0205 |
| 2021/0186648 A1 * | 6/2021 | Xia | G06T 7/20 |
| 2021/0255007 A1 * | 8/2021 | Hu | G01D 5/35361 |
| 2021/0282680 A1 * | 9/2021 | Rehan | A61B 5/1459 |
| 2021/0364669 A1 * | 11/2021 | Dusterhoft | E21B 43/26 |
| 2022/0047341 A1 * | 2/2022 | Larkin | B25J 9/1635 |

OTHER PUBLICATIONS

Swain et al., "Remote Magnetic Manipulation of a Wireless Capsule Endoscope in the Esophagus and Stomach of Humans (with videos)," Gastrointestinal Endoscopy, vol. 71, No. 7, Jun. 1, 2010, pp. 1290-1293, XP027062885, ISSN: 0016-5107, DOI: 10.1016/J.GIE. 2010.01.064.

China National Intellectual Property Administration, First Notification of Office Action and Search Report with English Translation, dated Jul. 28, 2023, regarding Application No. CN202010473394.8, 25 pages.

European Patent Office Communication, dated May 7, 2023, regarding Application No. EP20175491.8, 8 pages.

* cited by examiner

OPTICAL FIBER SENSOR SYSTEM

BACKGROUND INFORMATION

1. Field

The present disclosure relates generally to sensors and in particular, to fiber optic sensor systems. Still more particularly, the present disclosure relates to a method, apparatus, and system for a fiber optic sensor system that uses an optical fiber as a sensor.

2. Background

Detecting conditions in a system, such as a fluid system, such as a hydraulic fluid system or a person, can be challenging. For example, with a hydraulic fluid system that operates brakes in a vehicle, a soft brake pedal and rotor warping can result from low brake fluid pressure. The low brake fluid pressure can be caused by a number of different conditions in the hydraulic system. For example, water or air can cause low brake fluid pressure. A leak a brake line can also cause low brake fluid pressure. Determining cause of low brake fluid pressure can be more time-consuming than desired.

As another example, in some instances, diagnosing conditions in the gastrointestinal tract can be challenging with currently available techniques. In system in the form of a person, gastrointestinal symptoms such as heartburn, indigestion, dyspepsia, and bloating, can be common symptoms. These symptoms, however, can be misinterpreted. For example, heartburn involves a burning sensation in the chest or abdomen. This sensation is caused by gastroesophageal reflux in which acid from the stomach flows backwards up into the esophagus. If this condition occurs more than two times a week, a person may have gastroesophageal reflux disease. Additionally, heartburn is a common sign of acid reflux but does not appear in every case.

Performing different types of diagnostic tests is useful but only provide a snapshot for a particular time or short period of time of the gastrointestinal tract. The snapshots only rarely catch the occurrence of acid reflux in the person. As a result, the diagnosis of this and other types of conditions is made with a limited amount of information. This limited amount of information makes diagnosing different conditions more difficult.

Therefore, it would be desirable to have a method and apparatus that take into account at least some of the issues discussed above, as well as other possible issues. For example, it would be desirable to have a method and apparatus that overcome a technical problem with obtaining information needed to more accurately detect conditions in different systems.

SUMMARY

An example of the present disclosure provides an optical sensor system comprising a capsule, an optical fiber, an optical system, and a transmitter. The optical fiber is stored within the capsule. The optical fiber unfurls when the capsule travels through a tube system. The optical system is in the capsule and is connected to a proximal end of the optical fiber. The optical system sends optical signals through the optical fiber and detect response optical signals occurring in response to the optical signals sent through the optical fiber. The transmitter is in the capsule and is in communication with the optical system. The transmitter transmits sensor data based on the response optical signals detected by the optical system.

Another example of the present disclosure provides a capsule, an optical fiber, an optical system, and a transmitter. The optical fiber is stored within the capsule. The optical fiber unfurls from the capsule as the capsule travels in a tube system. The optical system is connected to a proximal end of the optical fiber. The optical system sends optical signals through the optical fiber and detects response optical signals occurring in response to the optical signals sent through the optical fiber. The transmitter is in communication with the optical system. The transmitter transmits sensor data based on the response optical signals detected by the optical system.

Yet another example of the present disclosure provides a method for delivering an optical sensor. A capsule is placed into a tube system, wherein an optical fiber is stored within the capsule. The capsule is moved through the tube system. The optical fiber is unfurled as the capsule travels through a tube system. Optical signals are sent through the optical fiber from a proximal end of the optical fiber. Response optical signals occurring in response to the optical signals sent through the optical fiber are detected. Sensor data is transmitted based on the response optical signals detected by the optical system.

The features and functions can be achieved independently in various examples of the present disclosure or may be combined in yet other examples in which further details can be seen with reference to the following description and drawings.

BRIEF DESCRIPTION OF THE DRAWINGS

The novel features believed characteristic of the illustrative examples are set forth in the appended claims. The illustrative examples, however, as well as a preferred mode of use, further objectives and features thereof, will best be understood by reference to the following detailed description of an illustrative example of the present disclosure when read in conjunction with the accompanying drawings, wherein:

DETAILED DESCRIPTION

The illustrative examples recognize and take into account one or more different considerations. For example, the illustrative examples recognize and take into account obtaining the desired amount of data over time is unachievable with currently used techniques. For example, a camera integrated within a capsule can placed into a fluid system, such as for example a hydraulic system or the capsule can be swallowed by a person. The camera operates to provide images or video as the capsule travels through the system for which information is desired, such as the hydraulic fluid system in a vehicle or the gastrointestinal tract in the person. The illustrative examples recognize and take into account that this type of data collection only provides images for a selected location for limited period of time.

The illustrative examples recognize and take into account that it would be desirable to have a sensor system that is capable of collecting data for a location for a longer period of time as compared to current techniques. Further, the illustrative examples recognize and take into account that it would be desirable to have a sensor system that can collect data for multiple locations in tube system such as a hydraulic system in a vehicle, a gastrointestinal tract in in a person, or tube systems in other types of mobile systems.

Thus, the illustrative examples provide a method, apparatus, and system for collecting sensor data using an optical sensor system with an optical fiber as a sensor to generate sensor data.

Figure 1:
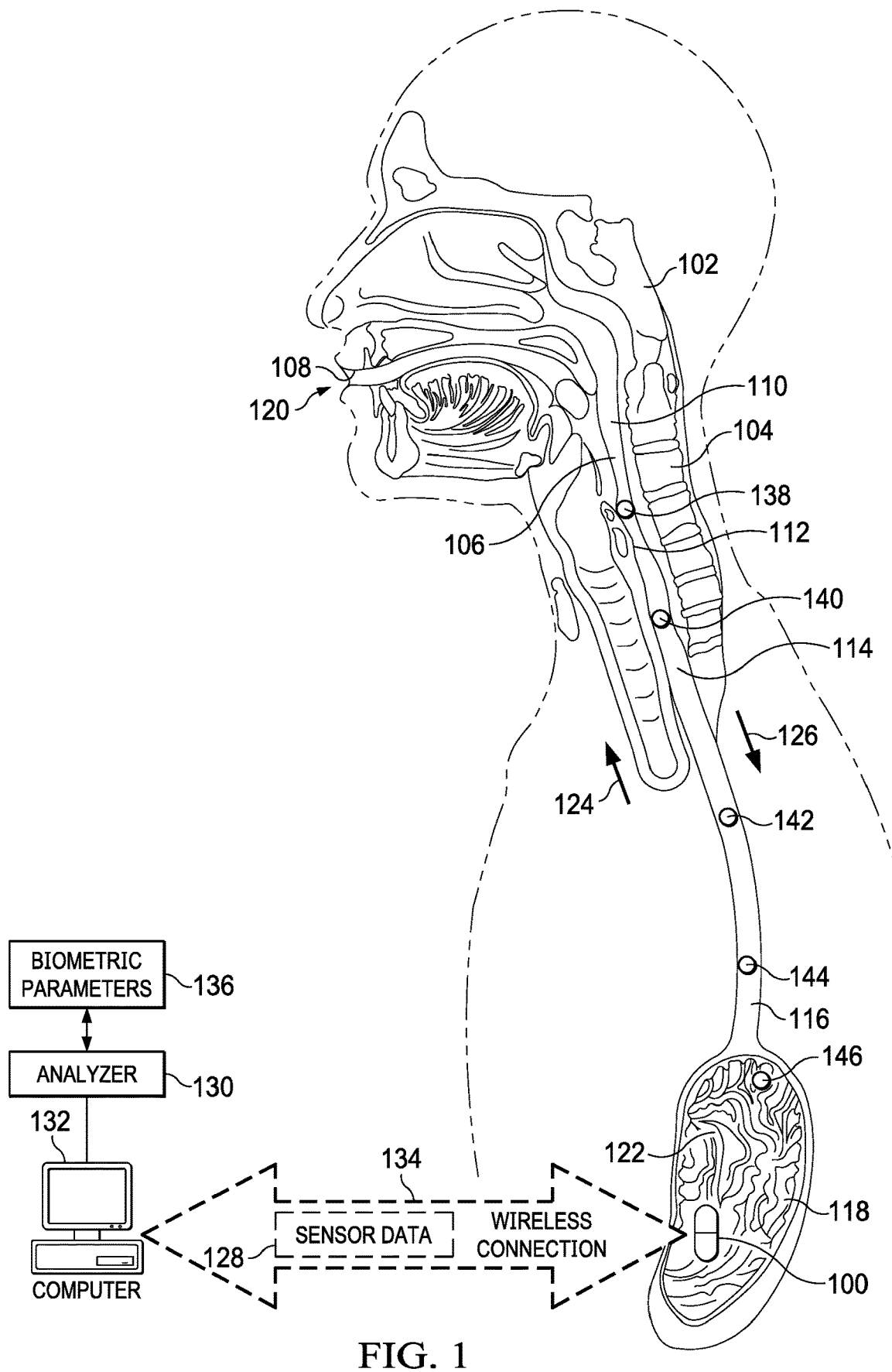
FIG. 1 is an illustration of a fiber optic sensor system in accordance with an illustrative example.

With reference to FIG. 1, an illustration of a fiber optic sensor system is depicted in accordance with an illustrative example. As depicted, capsule 100 has been swallowed by person 102. As capsule 100 travels down gastrointestinal tract 104, optical fiber 106 unfurls from capsule 100.

As depicted, optical fiber 106 has a core covered by a cladding with a lower index of refraction than the core such the optical fiber functions as a waveguide. In this illustrative example, optical fiber 106 can have a diameter that is the same or less than the diameter of a human hair. For example, optical fiber 106 can have a diameter from about 9 microns to about 175 microns.

As depicted in this figure, capsule 100 has traveled from mouth 108 past pharynx 110 and through upper esophagus sphincter 112, esophagus 114, and lower esophagus sphincter 116 into stomach 118. Distal end 120 of optical fiber 106 is anchored or held in mouth 108. Proximal end 122 of optical fiber 106 is connected to capsule 100.

In this illustrative example, capsule 100 transmits optical signals through optical fiber 106 in the direction of arrow 124. An optical system (not shown) in capsule 100 generates and transmits the optical signals These signals are reflected at distal end 120, which has a cladding to reflect light in this example. Response optical signals travel back through optical fiber 106 in the direction of arrow 126 to capsule 100. The optical system also detects the response optical signals in this example.

Capsule 100 generates sensor data 128 based on the response optical signals detected and transmits sensor data 128 to analyzer 130 in computer 132. Sensor data 128 is transmitted over wireless connection 134. Wireless connection 134 can be, for example, a Bluetooth connection, Wi-Fi connection, or some other suitable type of connection that uses wireless signals.

"Wi-Fi" is a trademark of the Wi-Fi alliance. Wi-Fi signals refer to radio frequency signals that are transmitted in a manner that follows a family of IEEE 802.11 standards. Bluetooth" is a trademark of Bluetooth SIG. Bluetooth refers to a standard for exchanging data between devices using ultrahigh frequency (UHF) radio frequency signals.

Analyzer 130 processes sensor data 128 to determine parameters 136. In this illustrative example, parameters 136 are biometric parameters because the system is person 102. These biometric parameters include, for example, at least one of a temperature, a pressure, a strain, a heart rate, a respiratory rate, a blood pressure, a heartbeat, a sound, or other information about person 102.

As used herein, the phrase "at least one of," when used with a list of items, means different combinations of one or more of the listed items can be used, and only one of each item in the list may be needed. In other words, "at least one of" means any combination of items and number of items may be used from the list, but not all of the items in the list are required. The item can be a particular object, a thing, or a category.

For example, without limitation, "at least one of item A, item B, or item C" may include item A, item A and item B, or item B. This example also may include item A, item B, and item C or item B and item C. Of course, any combinations of these items can be present. In some illustrative examples, "at least one of" can be, for example, without limitation, two of item A; one of item B; and ten of item C; four of item B and seven of item C; or other suitable combinations.

In this illustrative example, sensor data 128 can be detected and sent to analyzer 130 for analysis for longer periods of time as compared to current techniques. Further, sensor data 128 can be identified for various locations within gastrointestinal tract 104 from optical fiber 106. Based on time-of-flight and other information, parameters 136 can be determined from sensor data 128 in different locations such as location 138 in upper esophagus sphincter 112, location 140 in esophagus 114, location 142 in esophagus 114, location 144 in esophagus 114, and location 146 in stomach 118.

These locations are just some illustrative examples of locations and not meant to be limiting to what locations can be selected for determining sensor data 128. Parameters 136 can be determined for other locations in addition to or in place of these example locations.

Further, this example in FIG. 1 is only one example of how sensor data can be generates using an optical fiber 106. In another illustrative, the response optical signals can be detected at the distal end of optical fiber 106. In this example, the response optical signals are the optical signals when detected at the distal end. This type of detection can occur when an optical receiver is connected to the distal end of optical fiber 106 instead of being located in capsule 100. This configuration can be used when the distal end of optical fiber 106 remains in mouth 108 of person 102.

Figure 2:
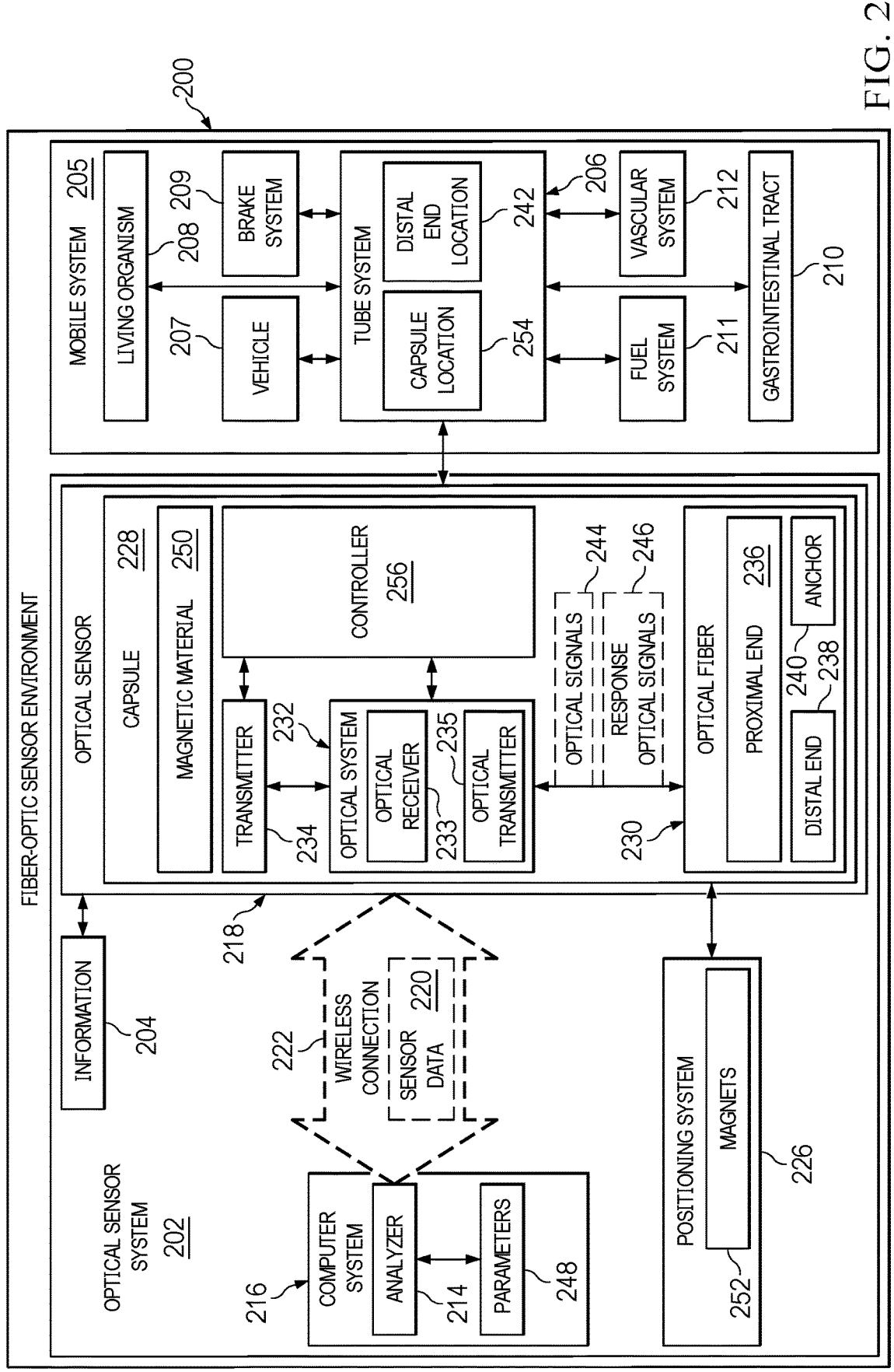
FIG. 2 is an illustration of a block diagram of a fiber optic sensor environment in accordance with an illustrative example.

With reference now to FIG. 2, an illustration of a block diagram of a fiber optic sensor environment is depicted in accordance with an illustrative example. As depicted, the components in FIG. 1 are examples of components that can be used in fiber-optic sensor environment 200.

As depicted, optical sensor system 202 can be used to generate information 204 about tube system 206. In the illustrative example, tube system 206 is a structure in mobile system 205. Mobile system 205 is a physical real-world system moves under its own locomotion.

In this illustrative example, mobile system 205 can be one of vehicle 207 and living organism 208. Tube system 206 is a canal, pipeline network, hose network, or continuous passageway through one of vehicle 207 and living organism 208. In the illustrative example, vehicle 207 can be an automobile, a truck, a sports car, an aircraft, an airplane, or some other vehicle. Living organism 208 can be, for example, a person, an animal, or some other type of living organism that has tube systems.

Tube system 208 can be comprised of pipes, tubes, hoses, valves, pumps, or other structures through which a fluid can flow from the stored when tube system 208 is in vehicle 207. For example, tube system 208 can be brake system 209, fuel system 211, or some other fluid or hydraulic system through which a fluid can flow in vehicle 207.

As another example, when located in living organism 208, tube system 206 can be comprised of organs and structures connecting organs. For example, tube system 206 can be gastrointestinal tract 210, vascular system 212, or some other passageway within living organism 208. Gastrointestinal tract 104 in person 102 in FIG. 1 is an example of gastrointestinal tract 210.

As depicted, optical sensor system 202 comprises a number of different components. In this illustrative example, optical sensor system 202 includes analyzer 214 in computer system 216 and optical sensor 218.

In this illustrative example, optical sensor 218 generates sensor data 220 and transmits sensor data 220 to analyzer 214 for processing. As depicted, information 204 in the form of sensor data 220 is sent over wireless connection 222. Wireless connection 222 facilitates transmitting wireless signals using a standard selected from at least one of Wi-Fi wireless signals, Bluetooth wireless signals, Zigbee wireless signals, or other suitable types of wireless signals.

"Zigbee" is a trademark of Zigbee Alliance. Zigbee refers to a standard for exchanging data between devices using wireless signals as defined by IEEE 802.15.4.

As depicted, optical sensor 218 is a hardware device that is designed and constructed to travel through tube system 206. Positioning system 226 is a hardware system that is part of optical sensor system 202 and may include software. Positioning system 226 operates to position optical sensor 218. This positioning of optical sensor 218 includes at least one of holding optical sensor 218 in a particular location in tube system 206 or moving optical sensor 218 through tube system 206.

Optical sensor 218 is comprised of a number of different components. As depicted, optical sensor 218 includes capsule 228, optical fiber 230, optical system 232, transmitter 234, and controller 256.

As depicted, capsule 228 is a physical housing for optical sensor 218. Capsule 220 has the size and shape suitable for traveling through tube system 206. Further, capsule 220 can be comprised of a material that is suitable for the fluid in which capsule 220 is immersed when placed into tube system 206. For example, capsule 228 can have a size and shape similar to pills that are taken orally by people when tube system 206 is located in a person. For example, capsule 228 can have a shape in the form of a disk, a spherocylinder, a sphere, or other shapes for use in tube system 206.

Optical fiber 230 is stored within capsule 228. Optical fiber 230 can be coiled, wound, or otherwise stored in capsule 228. The storage of optical fiber 230 is such that optical fiber 230 unfurls when capsule 228 travels through tube system 206. In other words, optical fiber 230 can deploy to unfold, unwind, or otherwise lengthen or extend from capsule 228.

As depicted, optical fiber 230 has proximal end 236 and distal end 238. Proximal end 236 is connected to capsule 228. In this example, proximal end 236 is connected to capsule 228 by being connected to optical system 232 located within capsule 228.

Different diameters can be selected for optical fiber 230 depending on mobile system 205. For example, when mobile system 205 is living organism 208, optical fiber 230 can have a diameter that is about the same or less than a human hair. For example, optical fiber 230 can have a diameter from about 9 microns to about 175 microns. In another example, when mobile system 205 is vehicle 207, optical fiber 230 can have a diameter from about 9 microns to about 250 microns. Of course, other diameters can be selected for optical fiber 230 depending on the particular type of tube system 206.

In this illustrative example, a portion or all of capsule 228 can be formed from magnetic material 250. As depicted, positioning system 226 can include a group of magnets 252. The group of magnets 252 can generate a magnetic field that is sufficient to position capsule 228 within tube system 206. The positioning can include at least one of holding capsule 228 at capsule location 254 or moving capsule 228 to capsule location 254 in tube system 206. As depicted, movement of the group of magnets 252 positions capsule 228 within tube system 206. Thus, the positioning of capsule 228 is based on the movement of the group of magnets 252.

In this illustrative example, anchor 240 is located at distal end 238. Anchor 240 is a structure that holds distal end 238 at distal end location 242 in tube system 206.

In this illustrative example, optical system 232 and transmitter 234 are located in capsule 228. In other illustrative examples, these components can be located external to capsule 228.

As depicted, optical system 232 is connected to an end of optical fiber 230. In this illustrative example, the end is proximal end 236 when optical system 232 is located within capsule 228. Optical system 232 includes optical transmitter 235 that operates to send optical signals 244 through optical fiber 230 and optical receiver 233 that operates to detect response optical signals 246 occurring in response to optical signals 244 sent through optical fiber 230.

Transmitter 234 is located within capsule 228 in this illustrative example and is in communication with optical system 232. In this illustrative example, transmitter 234 transmits sensor data 220 based on response optical signals 246 detected by optical system 232.

In one illustrative example, sensor data 220 is generated using response optical signals 246. In another illustrative example, sensor data 220 is based on a difference between optical signals 244 and response optical signals 246. In this illustrative example, sensor data 220 is digital data describing at least one of response optical signals 246 or the difference between optical signals 244 and response optical signals 246. For example, digital data can include intensity, wavelength, amplitude, or other suitable types of information that describes characteristics of at least one of response optical signals 246, optical signals 244, or the difference between optical signals 244 and response optical signals 246.

As depicted, controller 256 controls the operation of optical system 232 and transmitter 234. As depicted, controller 256 controls the sending of optical signals 244 through optical fiber 230. For example, controller 256 can wait a period of time to control optical system 232 to transmit optical signals 244. The period of time can be such that all of optical fiber 230 has been extended from capsule 228. In another example, the period of time can be when capsule 228 has reached capsule location 254.

Controller 256 can also control when transmitter 234 transmits sensor data 220. The transmission of sensor data 220 can be continuous, periodic, or non-periodic. When the transmission of sensor data 220 is non-periodic, the transmission can be in response to an event, such as when a selected amount of sensor data 220 is present.

In this illustrative example, analyzer 214 in computer system 216 is in communication with transmitter 234 and receives sensor data 220 from transmitter 234. As depicted, analyzer 214 generates a group of parameters 248 from sensor data 220. As used herein, a "group of" items when used with reference to items means one or more items. For example, a group of parameters 248 is one or more of parameters 248.

As depicted in this example, the group of parameters 248 is selected from at least one of a temperature, a pressure, a strain, a heart rate, a respiratory rate, a blood pressure, a heartbeat, a sound, or some other type of parameter for living organism 208. As another example, the group of parameters 248 can be selected from at least one of a pressure, a strain, a temperature, a sound, a vibration, a corrosion level or some other type of parameter in vehicle 207.

In the illustrative example, sounds can be actively filtered and analyzed using algorithms to create a profile of the data reflecting the information returned from optical sensor 218. This information can represent events occurring in vehicle 207. The events can be, for example, an engine starting, an application of a brake, a gear change, or other events in vehicle 207.

As another example, this information can represent events occurring in living organism 208. These events can be, for example, a heartbeat, an opening and closing of a valve, an occurrence of acid reflux, or other events that cause sounds in mobile system 205, such as living organism 208.

Further, from sensor data 220, a location can be determined for each biometric parameter in the group of parameters. This location can be determined using information such as time delay, and characteristics for optical signals 244.

Additionally, the group of parameters 248 can be detected in real time over a period of time. As result, issues derived from sensor data that is a snapshot of a particular time and location into system 206 is reduced using optical sensor system 202.

Analyzer 214 can be implemented in software, hardware, firmware or a combination thereof. When software is used, the operations performed by analyzer 214 can be implemented in program code configured to run on hardware, such as a processor unit. When firmware is used, the operations performed by analyzer 214 can be implemented in program code and data and stored in persistent memory to run on a processor unit. When hardware is employed, the hardware can include circuits that operate to perform the operations in analyzer 214.

In the illustrative examples, the hardware can take a form selected from at least one of a circuit system, an integrated circuit, an application specific integrated circuit (ASIC), a programmable logic device, or some other suitable type of hardware configured to perform a number of operations.

Computer system 216 is a physical hardware system and includes one or more data processing systems. When more than one data processing system is present in computer system 216, those data processing systems are in communication with each other using a communications medium. The communications medium can be a network. The data processing systems can be selected from at least one of a computer, a server computer, a tablet computer, or some other suitable data processing system.

Figure 3:
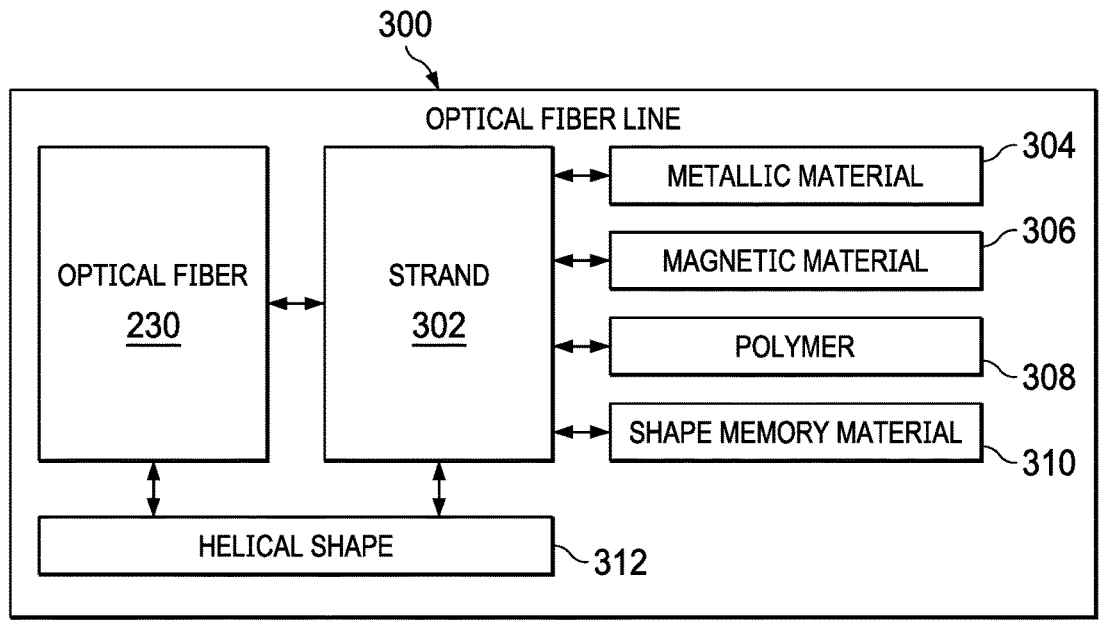
FIG. 3 is an illustration of a block diagram of an optical fiber line in accordance with an illustrative example.

With reference next to FIG. 3, an illustration of a block diagram of an optical fiber line is depicted in accordance with an illustrative example. In the illustrative examples, the same reference numeral may be used in more than one figure. This reuse of a reference numeral in different figures represents the same element in the different figures.

In this illustrative example, optical fiber line 300 comprises optical fiber 230 and strand 302 associated with optical fiber 230. Strand 302 can be comprised of at least one of metallic material 304, magnetic material 306, polymer 308, shape memory material 310, or other suitable materials.

As depicted, strand 302 can be associated with optical fiber 230 by being attached parallel to at least a portion of the optical fiber 230 or extending through the optical fiber 230.

When strand 302 includes magnetic material 306, optical fiber 230 in optical fiber line 300 can be positioned with respect to axes extending through tube system 206. An axis can be defined for a cross-section of tube system 206. The axis can be centrally located through the cross section. The direction of the axes change as tube system 206 bends, winds, or folds.

For example, optical fiber 230 in optical fiber line 300 can be positioned to an axial location using a group of magnets 252 in positioning system 226. With magnetic material 306 in strand 302, optical fiber 230, can be positioned, for example, against a wall on the particular side of tube system 206.

In one illustrative example, strand 302 can have helical shape 312. In the illustrative example, optical fiber 230 has the same shape as helical shape 312. In this illustrative example, helical shape 312 can enable storing optical fiber 230 in manner that takes up less space within capsule 228. Further, helical shape 312 for optical fiber 230 can also act as an insulator When strand 302 is comprised of shape memory material 310, strand 302 changes shape based on at least one of a change in temperature or more application of an electrical current. For example, helical shape 312 can be described as follows: $x(t)=\text{cosine }(t)$, $y(t)=\text{sine }(t)$, and $z(t)=t$. In this example, $z(t)$ is the distance or length along a z-axis extending centrally through helical shape 312.

In other words, the number of curves can be present within a particular z-axis length as compared to when the strand changes shape to reduce the number curves that causes helical shape 312 to be less tightly wound. The number of curves can be described by $x(t)$ which increases when helical shape 312 becomes less tightly wound.

Figure 4:
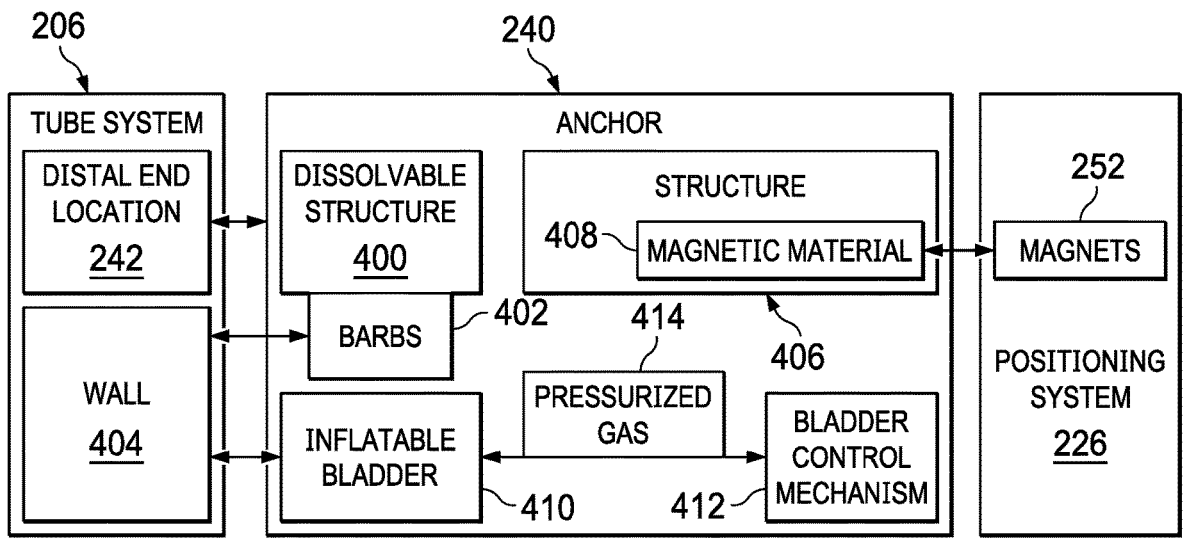
FIG. 4 is an illustration of an anchor in accordance with an illustrative example.

Turning next to FIG. 4, an illustration of an anchor is depicted in accordance with an illustrative example. As depicted, anchor 240 can take a number of different forms. For example, anchor 240 can be a dissolvable structure 400 with barbs 402. Barbs 402 can engage wall 404 of the tube system 206 to hold anchor 240 at distal end location 242.

In another illustrative example, anchor 240 is structure 406 that includes magnetic material 408. In this example, the group of magnets 252 in positioning system 226 can position anchor 240 at distal end location 242. A magnetic force applied to magnetic material 408 in anchor 240 can hold anchor 240 at distal end location 242. As yet another example, inflatable bladder 410 can be used to hold anchor 240 at distal end location 242. Inflatable bladder 410 can have a shape that allows fluid to flow through tube system 206 at distal end location 242 when inflatable bladder 410 is inflated. For example, inflatable bladder 410 can have a shape such as a doughnut, a shuttle cock, a helical shape, or some type of shape.

In still another illustrative example, anchor 240 can be located on or as part of capsule 228 instead of being located at distal end 238. In this illustrative example, anchor 240 comprises inflatable bladder 410. Inflatable bladder 410 is located on the exterior of capsule 228 and can be inflated and deflated by bladder control mechanism 412.

Bladder control mechanism 412 can operate using pressure pressurized gas 414. Bladder control mechanism 412 can be controlled by controller 256 or by wireless signals from an external control source.

In this depicted example, pressurized gas 414 can be generated by at least one of a chemical reaction or a pump within capsule 228.

When inflatable bladder 410 is inflated, at least one of inflatable bladder 410 or capsule 228 can be pressed against wall 404 of tube system such that capsule 228 remains at capsule location 254.

In one illustrative example, one or more technical solutions are present that overcome a technical problem with obtaining information needed to diagnose conditions. As a result, one or more technical solutions can provide a technical effect providing parameters for a mobile system through the use of an optical fiber extending through a tube system of mobile system such as a vehicle or a living organism.

In one illustrative example, a technical solution involves an optical fiber that unfurls from the capsule as the capsule travels through tube system in a vehicle or a living organism. An optical system in the capsule transmits optical signals and detects response optical signals in the optical fiber.

As depicted, sensor data is generated from at least one of using both the optical signals and the response optical signals or using the response optical signals. The sensor data can be transmitted for analysis. The generated sensor data can be provided for longer periods of time than currently used techniques.

Further, the optical signals in the response optical signals can be analyzed to determine where changes to optical signals occurred along the length of the optical fiber. The location of the changes is associated with parameters determined for a vehicle or a living organism based on the location where particular response optical signals in response to the optical signals occurred.

The illustration of fiber-optic sensor environment 200 and the different components in fiber-optic sensor environment 200 in FIG. 2-4 is not meant to imply physical or architectural limitations to the manner in which an illustrative example may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative example.

For example, one or more optical sensors in addition to or in place of optical sensor 218 may be present in optical sensor system 202. These different sensors may be introduced into tube system 206 or other tube systems in fiber-optic sensor environment 200.

As yet another example, one or more additional optical fibers can be connected to optical system 232 in capsule 228 in addition to optical fiber 230. In yet another example, transmitter 234 can be implemented within another component in optical sensor 218 such as optical system 232 or controller 256.

Figure 5:
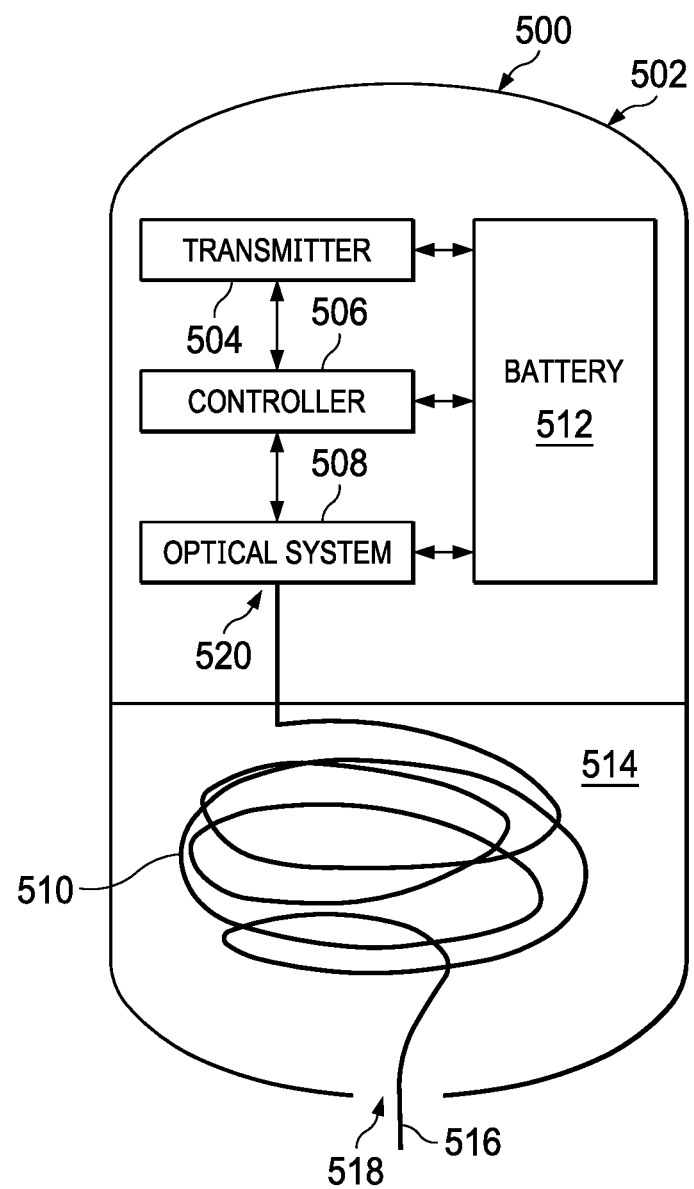
FIG. 5 is an illustration of an optical sensor in accordance with an illustrative example.

Turning now to FIG. 5, an illustration of an optical sensor is depicted in accordance with an illustrative example. As depicted, optical sensor 500 is an example of an implementation of optical sensor 218 shown in block form in FIG. 2. In this illustrative example, optical sensor comprises capsule 502, transmitter 504, controller 506, optical system 508, optical fiber 510, and battery 512.

Capsule 502 is an example of one implementation for capsule 228 shown in block form in FIG. 2. In this example, capsule 502 is a spherocylinder shaped housing with cavity 514. The other components of optical sensor 500 are located within cavity 514 inside of capsule 502.

Transmitter 504 can transmit wireless signals with sensor data. Optical system 508 transmits optical signals through optical fiber 510 and detects response optical signals in optical fiber 510. Optical system 508 can generate sensor data that is transmitted by transmitter 504.

In this illustrative example, controller 506 controls the operation of transmitter 504 and optical system 508. Battery 512 provides power to operate transmitter 504, controller 506, and optical system 508.

As depicted, optical fiber 510 is stored in cavity 514 within capsule 502. Distal end 516 of optical fiber 510 can unfurl through opening 518 in 502 while traveling through a tube system. In other words, distal end 516 can be deployed through opening 518 such that optical fiber 510 unfurls to extend from capsule 502. Proximal end 520 of optical fiber 510 is connected to optical system 508.

Figure 6:
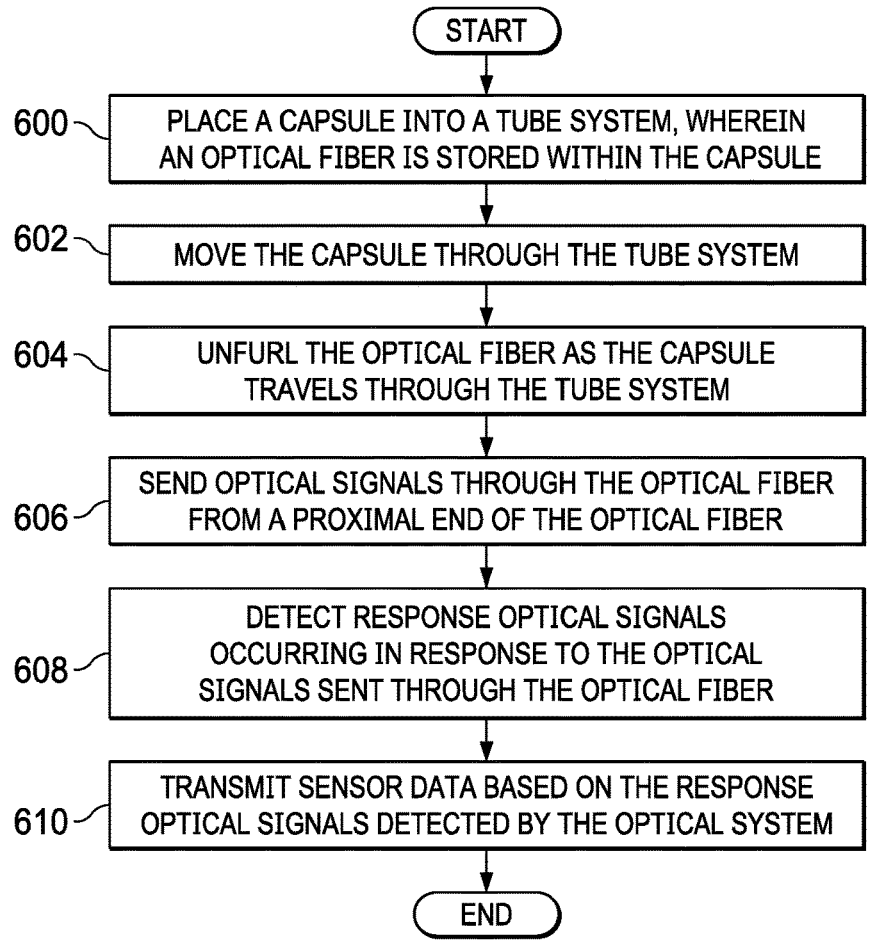
FIG. 6 is an illustration of a flowchart of a process for operating an optical sensor in accordance with an illustrative example.

Turning next to FIG. 6, an illustration of a flowchart of a process for operating an optical sensor is depicted in accordance with an illustrative example. The process illustrated in FIG. 6 can be implemented using optical sensor system 202 in FIG. 2.

The process beings by placing a capsule into a tube system, wherein an optical fiber is stored within the capsule (operation 600). The process moves the capsule through the tube system (operation 602). The process unfurls the optical fiber as the capsule travels through a tube system (operation 604).

The process sends optical signals through the optical fiber from a proximal end of the optical fiber (operation 606). The process detects response optical signals occurring in response to the optical signals sent through the optical fiber (operation 608). The process transmits sensor data based on the response optical signals detected by the optical system (operation 610). The process terminates thereafter.

Figure 7:
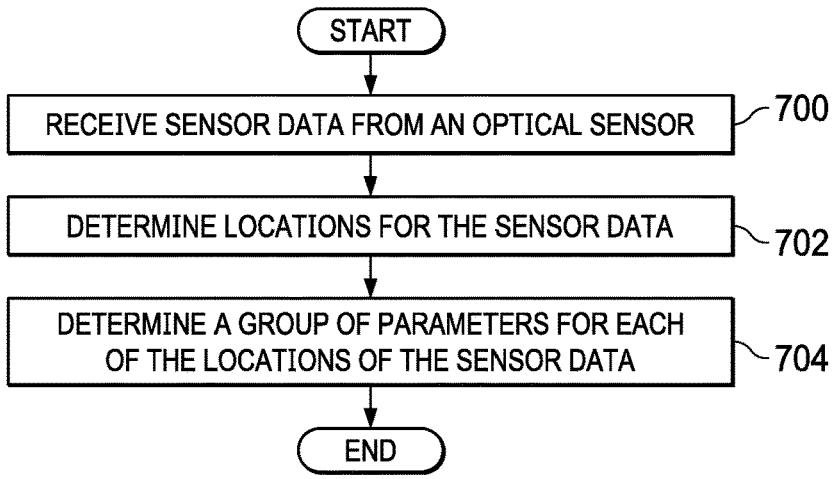
FIG. 7 is an illustration of a flowchart of a process for determining parameters in accordance with an illustrative example.

With reference next to FIG. 7, an illustration of a flowchart of a process for determining parameters is depicted in accordance with an illustrative example. The process in FIG. 7 can be implemented in hardware, software, or both. When implemented in software, the process can take the form of program code that is run by one of more processor units located in one or more hardware devices in one or more computer systems. For example, the process can be implemented in analyzer 214 in computer system 216 in FIG. 2.

The process begins by receiving sensor data from an optical sensor (operation 700). In operation, 700, the sensor data is for a vehicle or a living organism and can be received from an optical sensor implementing the process illustrated in FIG. 6.

The process determines locations for the sensor data (operation 702). In operation 702, the time of flight and the length of the optical fiber is known. The time of flight can be determined from sensor data about response optical signals in this illustrative example. With this information, a location along the optical fiber can be correlated with a portion of the response optical signal.

The process determines a group of parameters for each of the locations of the sensor data (operation 704). The process terminates thereafter. In operation 704, the characteristics of the response optical signal at the location can be analyzed to determine the parameters.

In this illustrative example, sensor data can comprise the response optical signals, the optical signals and the response optical signals, a difference between the optical signals and the response optical signals, or other suitable information. Further, the sensor data also can include the timestamp or other information that can be used to determine when particular portions of the optical signals were sent or received. This timestamp information can be used to determine time-of-flight for use in determining the location along the optical fiber that was the source for particular portions of the response optical signals. In this example, optical signals become response optical signals when the optical signals are detected.

The flowcharts and block diagrams in the different depicted examples illustrate the architecture, functionality, and operation of some possible implementations of apparatuses and methods in an illustrative example. In this regard, each block in the flowcharts or block diagrams can represent at least one of a module, a segment, a function, or a portion of an operation or step. For example, one or more of the blocks can be implemented as program code, hardware, or a combination of the program code and hardware. When implemented in hardware, the hardware can, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams can be implemented using special purpose hardware systems that perform the different operations or combinations of special purpose hardware and program code run by the special purpose hardware.

In some alternative implementations of an illustrative example, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram.

Figure 8:
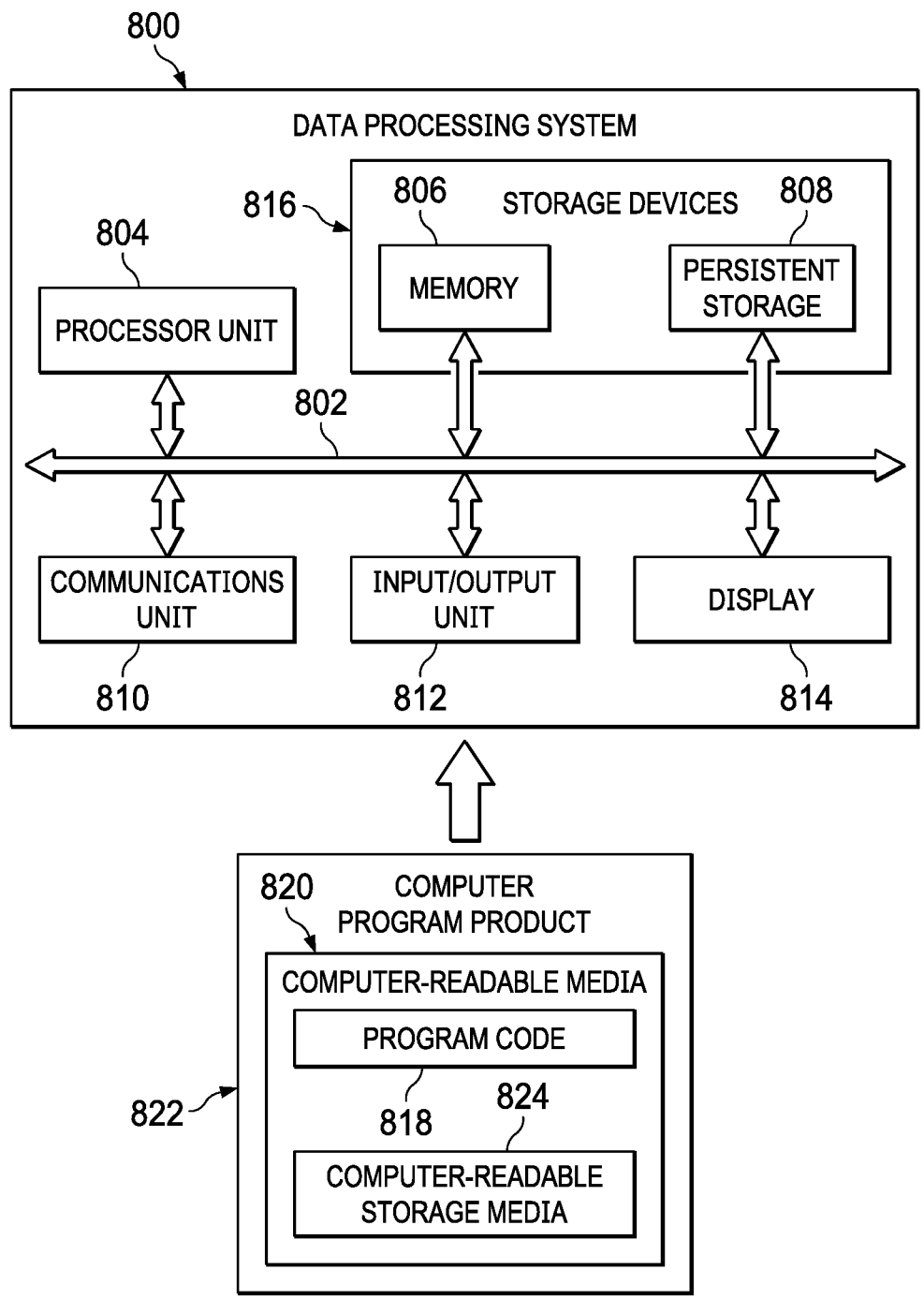
FIG. 8 is an illustration of a block diagram of a data processing system in accordance with an illustrative example.

Turning now to FIG. 8, an illustration of a block diagram of a data processing system is depicted in accordance with an illustrative example. Data processing system 800 can be used to implement computer system 216. In this illustrative example, data processing system 800 includes communications framework 802, which provides communications between processor unit 804, memory 806, persistent storage 808, communications unit 810, input/output (I/O) unit 812, and display 814. In this example, communications framework 802 takes the form of a bus system.

Processor unit 804 serves to execute instructions for software that can be loaded into memory 806. Processor unit 804 includes one or more processors. For example, processor unit 804 can be selected from at least one of a multicore processor, a central processing unit (CPU), a graphics processing unit (GPU), a physics processing unit (PPU), a digital signal processor (DSP), a network processor, or some other suitable type of processor.

Memory 806 and persistent storage 808 are examples of storage devices 816. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 816 may also be referred to as computer-readable storage devices in these illustrative examples. Memory 806, in these examples, can be, for example, a random-access memory or any other suitable volatile or non-volatile storage device. Persistent storage 808 can take various forms, depending on the particular implementation.

For example, persistent storage 808 may contain one or more components or devices. For example, persistent storage 808 can be a hard drive, a solid-state drive (SSD), a flash memory, a rewritable optical disk, a rewritable magnetic tape, or some combination of the above. The media used by persistent storage 808 also can be removable. For example, a removable hard drive can be used for persistent storage 808.

Communications unit 810, in these illustrative examples, provides for communications with other data processing systems or devices. In these illustrative examples, communications unit 810 is a network interface card.

Input/output unit 812 allows for input and output of data with other devices that can be connected to data processing system 800. For example, input/output unit 812 can provide a connection for user input through at least one of a keyboard, a mouse, or some other suitable input device. Further, input/output unit 812 can send output to a printer. Display 814 provides a mechanism to display information to a user.

Instructions for at least one of the operating system, applications, or programs can be located in storage devices 816, which are in communication with processor unit 804 through communications framework 802. The processes of the different examples can be performed by processor unit 804 using computer-implemented instructions, which can be located in a memory, such as memory 806.

These instructions are referred to as program code, computer usable program code, or computer-readable program code that can be read and executed by a processor in processor unit 804. The program code in the different examples can be embodied on different physical or computer-readable storage media, such as memory 806 or persistent storage 808.

Program code 818 is located in a functional form on computer-readable media 820 that is selectively removable and can be loaded onto or transferred to data processing system 800 for execution by processor unit 804. Program code 818 and computer-readable media 820 form computer program product 822 in these illustrative examples. In the illustrative example, computer-readable media 820 is computer-readable storage media 824.

In these illustrative examples, computer-readable storage media 824 is a physical or tangible storage device used to store program code 818 rather than a medium that propagates or transmits program code 818.

Alternatively, program code 818 can be transferred to data processing system 800 using a computer-readable signal media. The computer-readable signal media can be, for example, a propagated data signal containing program code 818. For example, the computer-readable signal media can be at least one of an electromagnetic signal, an optical signal, or any other suitable type of signal. These signals can be transmitted over connections, such as wireless connections, optical fiber cable, coaxial cable, a wire, or any other suitable type of connection.

The different components illustrated for data processing system 800 are not meant to provide architectural limitations to the manner in which different examples can be implemented. In some illustrative examples, one or more of the components may be incorporated in or otherwise form a portion of, another component. For example, memory 806, or portions thereof, can be incorporated in processor unit 804 in some illustrative examples. The different illustrative examples can be implemented in a data processing system including components in addition to or in place of those illustrated for data processing system 800. Other components shown in FIG. 8 can be varied from the illustrative examples shown. The different examples can be implemented using any hardware device or system capable of running program code 818.

Thus, the illustrative examples provide a method, an apparatus, and a system for delivering an optical sensor into a tube system to generate sensor data. A capsule is placed into a tube system. An optical fiber is stored within the capsule. The capsule is moved through the tube system. The optical fiber is unfurled as the capsule travels through the tube system. Optical signals are sent through the optical fiber from a proximal end of the optical fiber. Response optical signals occurring in response to the optical signals sent through the optical fiber are detected. Sensor data is transmitted based on the response optical signals detected by the optical sensor.

The illustrative example employs an optical sensor system in which an optical sensor employs an optical fiber as a sensor that can monitor many processes throughout a system such as a vehicle, an unmanned vehicle, or a living organism when deployed in the tube system in the vehicle or the living organism. The monitoring may include detecting parameters such as temperature, heat, sounds, vibrations, recorded along the length of the optical fiber. The illustrative examples enable localized accuracy regarding where the event occurred along the length of the optical fiber.

The description of the different illustrative examples has been presented for purposes of illustration and description and is not intended to be exhaustive or limited to the examples in the form disclosed. The different illustrative examples describe components that perform actions or operations. In an illustrative example, a component can be configured to perform the action or operation described. For example, the component can have a configuration or design for a structure that provides the component an ability to perform the action or operation that is described in the illustrative examples as being performed by the component.

Many modifications and variations will be apparent to those of ordinary skill in the art. Further, different illustrative examples may provide different features as compared to other desirable examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. An optical sensor system comprising:
    an optical sensor, the optical sensor comprising:
        a capsule;
        an optical fiber stored within the capsule, wherein a distal end of the optical fiber extends from the capsule and is anchored at a distal end location of a tube system, the optical fiber unfurls from the capsule as the optical sensor travels through the tube system;
        an optical system in the capsule, wherein the optical system is connected to a proximal end of the optical fiber and sends optical signals through the optical fiber and detects response optical signals occurring in response to the optical signals sent through the optical fiber; and
        a transmitter in the capsule and in communication with the optical system, wherein the transmitter transmits sensor data based on the response optical signals detected by the optical system.

2. The optical sensor system of claim 1 further comprising:
    a magnetic material associated with the capsule; and
    a positioning system comprising a group of magnets moveable externally to the tube system, wherein movement of the group of magnets positions the capsule within the tube system.

3. The optical sensor system of claim 1, wherein the optical sensor further comprises:
    an anchor at the distal end of the optical fiber, wherein the anchor is a structure that holds the distal end at the distal end location of the tube system.

4. The optical sensor system of claim 3, wherein the anchor is a dissolvable structure with barbs, wherein the barbs engage a wall of the tube system to hold the anchor at the distal end location of the tube system.

5. The optical sensor system of claim 3, wherein the anchor is the structure with a magnetic material or a magnet, wherein a magnetic force holds the anchor at the distal end location of the tube system.

6. The optical sensor system of claim 1, wherein the optical sensor further comprises:
    a strand associated with the optical fiber.

7. The optical sensor system of claim 6, wherein the strand is associated with the optical fiber by being attached in parallel to at least a portion of the optical fiber or extending through the optical fiber.

8. The optical sensor system of claim 6, wherein the strand is comprised of at least one of a metallic material, polymer, shape memory material, or a magnetic material.

9. The optical sensor system of claim 6, wherein the strand has a helical shape causing the optical fiber to have the helical shape.

10. The optical sensor system of claim 9, wherein the strand is comprised of a shape memory material.

11. The optical sensor system of claim 1, wherein the sensor data is the response optical signals.

12. The optical sensor system of claim 1, wherein the sensor data is a difference between the optical signals and the response optical signals.

13. The optical sensor system of claim 1 further comprising:
    an analyzer in a computer system, wherein the analyzer is in communication with the transmitter, wherein the analyzer generates a group of parameters from the sensor data.

14. The optical sensor system of claim 13, wherein the group of parameters is selected from at least one of a temperature, a pressure, a strain, a sound, or a vibration.

15. The optical sensor system of claim 13, wherein a location is determined for each parameter in the group of parameters.

16. The optical sensor system of claim 1 further comprising:
    the tube system which the optical sensor is anchored to and travels through, wherein the tube system is one of a hydraulic system and a fuel system.

17. The optical sensor system of claim 1, wherein the tube system is located in one of a vehicle, a living organism, an automobile, a truck, a sports car, an aircraft, and an airplane.

18. The optical sensor system of claim 1 further comprising:
  a controller in the capsule, wherein the controller controls when the optical system sends the optical signals through the optical fiber.

19. An optical sensor system comprising:
  an optical sensor, the optical sensor comprising:
    a capsule;
    an optical fiber stored within the capsule, wherein a distal end of the optical fiber extends through an opening in the capsule and is anchored at a distal end location of a tube system, the optical fiber unfurls from the capsule through the opening in the capsule as the optical sensor travels in the tube system;
    an optical system connected to a proximal end of the optical fiber, wherein the optical system sends optical signals through the optical fiber and detects response optical signals occurring in response to the optical signals sent through the optical fiber; and
    a transmitter in communication with the optical system, wherein the transmitter transmits sensor data based on the response optical signals detected by the optical system.

20. The optical sensor system of claim 19, wherein the optical system is located in the capsule and the transmitter is located within the capsule, wherein the transmitter transmits the sensor data using a wireless connection.

21. The optical sensor system of claim 19, wherein the optical sensor further comprises:
  an optical receiver in the optical system connected to the distal end of the optical fiber.

22. The optical sensor system of claim 19, wherein the proximal end of the optical fiber is connected to an optical transmitter in the optical system that sends the optical signals through the optical fiber and wherein the distal end of the optical fiber is connected to an optical receiver in the optical system that detects the response optical signals occurring in response to the optical signals sent through the optical fiber.

23. A method for delivering an optical sensor comprising:
  placing a capsule into a tube system, wherein an optical fiber is stored within the capsule, wherein a distal end of the optical fiber extends through an opening in the capsule and is anchored at a distal end location of the tube system;
  moving the capsule through the tube system,
  unfurling the optical fiber through the opening in the capsule as the capsule travels through the tube system;
  sending optical signals from an optical system connected to a proximal end of the optical fiber in the capsule, the optical signals sent through the optical fiber from the proximal end of the optical fiber;
  detecting response optical signals occurring in response to the optical signals sent through the optical fiber; and
  transmitting sensor data with a transmitter in the capsule, the sensor data based on the response optical signals detected by the optical sensor.

24. The method of claim 23, wherein a magnet material is associated with the capsule and further comprising:
  moving a group of magnets external to the tube system, wherein the capsule is positioned within the tube system based on a movement of the group of magnets.

25. The method of claim 23 further comprising:
  holding the distal end of the optical fiber at the distal end location of the tube system with an anchor, wherein the anchor is a structure that holds the distal end at the distal end location of the tube system.

26. The method of claim 25, wherein the anchor is the structure with a magnetic material or a magnet, wherein a magnetic force holds the anchor at the distal end location of the tube system.

27. The method of claim 23, wherein a strand is associated with the optical fiber.

28. The method of claim 27, wherein the strand is associated with the optical fiber by being attached in parallel to at least a portion of the optical fiber or extending through the optical fiber.

29. The method of claim 27, wherein the strand is comprised of at least one of a metallic material, polymer, shape memory material, or a magnetic material.

30. The method of claim 27, wherein the strand has a helical shape causing the optical fiber to have the helical shape.

31. The method of claim 30, wherein the strand is comprised of a shape memory material.

32. The method of claim 30 further comprising:
  positioning the optical fiber to an axial location using a group of magnets.

33. The method of claim 23, wherein the sensor data is the optical response signals.

34. The method of claim 23, wherein the sensor data comprises a difference between the optical signals and the response optical signals.

35. The method of claim 23 further comprising:
  determining a group of parameters using the sensor data.

36. The method of claim 35, wherein the group of parameters is selected from at least one of a temperature, a pressure, a strain, a sound, or a vibration.

37. The method of claim 36, wherein a location is determined for each parameter in the group of parameters.

38. The method of claim 23, wherein the tube system is one of a hydraulic system and a fuel system.

39. The method of claim 23, wherein the tube system is located in one of a vehicle, a living organism, an automobile, a truck, a sports car, an aircraft, and an airplane.

* * * * *